(12) United States Patent
Beck et al.

(10) Patent No.: US 8,905,925 B2
(45) Date of Patent: Dec. 9, 2014

(54) CARDIAC REHABILITATION USING PATIENT MONITORING DEVICES

(75) Inventors: Kenneth C. Beck, St. Paul, MN (US); Ramesh Wariar, Blaine, MN (US); Viktoria A. Averina, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1041 days.

(21) Appl. No.: 12/482,172

(22) Filed: Jun. 10, 2009

(65) Prior Publication Data
US 2010/0016678 A1 Jan. 21, 2010

Related U.S. Application Data

(60) Provisional application No. 61/080,896, filed on Jul. 15, 2008.

(51) Int. Cl.
*A61B 5/00* (2006.01)
(Continued)

(52) U.S. Cl.
CPC ............... *A61B 5/222* (2013.01); *G06F 19/36* (2013.01); *A61B 5/0205* (2013.01);
(Continued)

(58) Field of Classification Search
CPC .............. A61B 5/11; A61B 5/4833–5/4836; A61B 5/0205; A61B 5/7475; A61B 5/02438–5/02444; A61B 5/0002; A61N 1/362; A61N 1/37247; A63B 2230/08–2230/105; A63B 2225/50; A63B 2213/004; G06F 19/36–19/366; G06F 19/3406; G06F 19/3418; G06F 19/3425; G06F 19/3475; G06F 19/3487
USPC .......... 600/300–301, 363–365, 373–374, 600/377–379, 382–384, 386–394, 481, 485, 600/500–503, 509, 515–519, 529–531, 600/544–547, 549; 128/920–925; 705/2–3; 482/1–9
See application file for complete search history.

(56) References Cited

U.S. PATENT DOCUMENTS 5,044,365 A * 9/1991 Webb et al. .................. 607/18
5,216,597 A * 6/1993 Beckers ........................ 356/39
(Continued)

OTHER PUBLICATIONS

"Cardiac Rehabilitation—Health Library", [online]. [retrieved Mar. 25, 2008]. Retrieved from the Internet: <URL: http://yourhealth.healtheast.org/library/healthguide/en-us/illnessconditions/topic.asp?hwid=support/hw230032>, (© 1995-2008 Heathwise, Incorporated), 4 pgs.

(Continued)

*Primary Examiner* — William Thomson
*Assistant Examiner* — Marie Archer
(74) *Attorney, Agent, or Firm* — Schwegman Lundberg & Woessner, P.A.

(57) ABSTRACT

Systems and methods permit remotely-monitored rehabilitation of a patient. A system can comprise a patient monitor configured to monitor a patient's physiological data. The patient monitor can monitor using a first monitoring mode. A patient communication device can be configured to present, to the patient, an option to perform an exercise regimen, and to receive a response indicating whether the patient will perform the exercise regimen. A configuration module coupled to the patient communication device can be configured to activate a second monitoring mode when the response indicates that the patient will perform the exercise regimen. When the exercise regimen is complete, the first monitoring mode can be re-established. When the response indicates that the patient will not perform the exercise regimen, the response can be recorded as a negative response, and the option to perform the exercise regimen can be presented again.

29 Claims, 8 Drawing Sheets

(51) Int. Cl.
*A61B 5/22* (2006.01)
*A61B 5/0205* (2006.01)
*A61N 1/372* (2006.01)
*A61N 1/362* (2006.01)
*A61N 1/00* (2006.01)
*G06F 19/00* (2011.01)

(52) U.S. Cl.
CPC .......... *A63B 2230/08* (2013.01); *A61B 5/0031* (2013.01); *G06F 19/3475* (2013.01); *G06F 19/3406* (2013.01); *A61B 5/0022* (2013.01); *A61N 1/37247* (2013.01); *A61B 5/4833* (2013.01); *G06F 19/3418* (2013.01); *G06F 19/3425* (2013.01); *A61N 1/362* (2013.01); *Y10S 482/902* (2013.01)
USPC .......... 600/300; 600/301; 600/372; 600/373; 600/374; 600/509; 705/2; 705/3; 482/8; 482/9; 482/902; 607/9; 607/32; 607/77

(56) References Cited

U.S. PATENT DOCUMENTS

| | | | |
|---|---|---|---|
| 5,474,090 A | 12/1995 | Begun et al. | |
| 5,538,007 A | 7/1996 | Gorman | |
| 5,591,104 A | 1/1997 | Andrus et al. | |
| 5,598,849 A | 2/1997 | Browne | |
| 5,810,747 A | 9/1998 | Brudny et al. | |
| 6,503,173 B2 | 1/2003 | Clem | |
| 6,626,800 B1 | 9/2003 | Casler | |
| 7,024,369 B1* | 4/2006 | Brown et al. | 705/2 |
| 2002/0058877 A1 | 5/2002 | Baumann et al. | |
| 2002/0198473 A1 | 12/2002 | Kumar et al. | |
| 2004/0102683 A1 | 5/2004 | Khanuja et al. | |
| 2004/0117214 A1* | 6/2004 | Shea | 705/2 |
| 2005/0065443 A1* | 3/2005 | Ternes | 600/509 |
| 2006/0064030 A1* | 3/2006 | Cosentino et al. | 600/547 |
| 2007/0061393 A1 | 3/2007 | Moore | |
| 2007/0100666 A1 | 5/2007 | Stivoric et al. | |
| 2007/0155588 A1* | 7/2007 | Stark et al. | 482/8 |
| 2007/0219059 A1 | 9/2007 | Schwartz et al. | |
| 2007/0244402 A1* | 10/2007 | Brockway et al. | 600/509 |
| 2009/0023555 A1* | 1/2009 | Raymond | 482/9 |
| 2009/0156908 A1* | 6/2009 | Belalcazar et al. | 600/301 |
| 2009/0171227 A1* | 7/2009 | Dziubinski et al. | 600/516 |
| 2009/0326356 A1* | 12/2009 | Kracker | 600/363 |

OTHER PUBLICATIONS

"Home program for cardiac rehabilitation—Health Library", [online]. [retrieved Mar. 25, 2008]. Retrieved from the Internet: <URL: http://yourhealth.healtheast.org/library/healthguide/en-us/support/topic.asp?hwid=hw230402>, (© 1995-2008 Heathwise, Incorporated), 2 pgs.

"Phase II of cardiac rehabilitation—Health Library", [online]. [retrieved Mar. 25, 2008]. Retrieved from the Internet: <URL: http://yourhealth.healtheast.org/library/healthguide/en-us/support/topic.asp?hwid=hw230413>, (© 1995-2008 Healthwise, Incorporated), 2 pgs.

"Phase III of cardiac rehabilitation—Health Library", [online]. [retrieved Mar. 25, 2008]. Retrieved from the Internet: <URL: http://yourhealth.healtheast.org/library/healthguide/en-us/support/topic.asp?hwid=hw230424>, (© 1995-2008 Healthwise, Incorporated), 2 pgs.

"Recommendations for exercise training in chronic heart failure patients.", *Eur Heart J.*, 22(2), Author—Working Group on Cardiac Rehabilitation & Exercice Physiology and Working Group on Heart Failure of the European Society of Cardiology., (Jan. 2001), 125-35.

De Lusignan, S., et al., "Compliance and effectiveness of 1 year's home telemonitoring. The report of a pilot study of patients with chronic heart failure.", *Eur J Heart Fail.*, 3(6), (Dec. 2001), 723-730.

Pina, I., et al., "Exercise and Heart Failure: A Statement From the American Heart Association Committee on Exercise, Rehabilitation, and Prevention", *Circulation*, 107, (2003), 1210-1225.

Reindl, I., et al., "Exertional hyperpnea in patients with chronic heart failure is a reversible cause of exercise intolerance.", *Basic Res Cardiol.*, 91 Suppl 1, (1996), 37-43.

* cited by examiner

CARDIAC REHABILITATION USING PATIENT MONITORING DEVICES

CROSS-REFERENCE TO RELATED APPLICATION

This application claims the benefit of U.S. Provisional Application No. 61/080,896, filed on Jul. 15, 2008, under 35 U.S.C. §119(e), which is hereby incorporated by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2008, Cardiac Pacemakers, Inc. All Rights Reserved.

BACKGROUND

Implantable medical devices (IMDs), including cardiac rhythm management devices such as pacemakers and implantable cardioverter/defibrillators, typically have the capability to communicate with an external device, such as an external programmer, via wireless telemetry, such as a radio-frequency (RF) or other telemetry link. While an external programmer is typically provided to program and modify the operating parameters of an IMD, modern IMDs also include the capability for bidirectional communication so that information, such as physiological data, can be transmitted to the programmer. Home health care remote monitoring systems can also communicate with the IMD and collect the patient and patient-related data.

In addition, some monitoring systems can also collect other objective or subjective data using additional external sensors, such as a blood pressure cuff, a weight scale, or a specialized device that prompts the patient with questions regarding their health state. Some home health care monitoring systems can communicate with a centralized or other remote system. Centralized systems, including medical practice systems, provide an efficient mode for physicians and other medical practitioners to manage patient-related data.

OVERVIEW

Example 1 describes a system comprising a patient monitor configured to monitor a patient's physiological data, including using a first monitoring mode; a patient communication device configured to: present, to a patient, an option to perform an exercise regimen; and receive a response from the patient indicating whether the patient will perform the exercise regimen; and a configuration module, coupled to the patient communication device, the configuration module configured to, when the response indicates that the patient will perform the exercise regimen: activate a second monitoring mode; detect that the exercise regimen is complete; and re-establish the first monitoring mode after the exercise regimen is complete; and when the response indicates that the patient will not perform the exercise regimen: record the response as a negative response; and repeat presenting the option to perform the exercise regimen to the patient.

In Example 2, the system of example 1 is optionally configured such that the patient monitor is configured to monitor the patient's physiological data repeatedly at intervals of time.

In Example 3, the system of any one or more of Examples 1 or 2 are optionally configured such the patient monitor includes an implantable medical device.

In Example 4, the system of any one or more of Examples 1-3 are optionally configured such that the patient monitor is configured to receive the patient's physiological data at a central system; and store the patient's physiological data at the central system.

In Example 5, the system of any one or more of Examples 1-4 are optionally configured such that the configuration module is configured to detect that the exercise regimen is complete by receiving an indication from the patient that the patient has completed exercising.

In Example 6, the system of any one or more of Examples 1-5 are optionally configured such that the configuration module is configured to use patient physiological data sensed in the second monitoring mode to determine that the patient has completed exercising.

In Example 7, the system of any one or more of Examples 1-6 are optionally configured comprising a clinician communication device, coupled to the patient communication device, and configured to: present, to a clinician, the patient's physiological data captured during the first and second monitoring modes; receive a clinician message from the clinician, the clinician message being in response to the presentation of the patient's physiological data; and communicate with patient communication device to revise at least one of the exercise regimen or the second monitoring mode based on the clinician message.

In Example 8, the system of any one or more of Examples 1-7 are optionally configured such that the patient communication device revises the exercise regimen by revising at least one of: an intensity of an exercise, a frequency of an exercise, a duration of an exercise, a type of exercise, or a specified exercise.

In Example 9, the system of any one or more of Examples 1-8 are optionally configured such that the patient monitor uses the clinician message to revise an aspect of the second monitoring mode corresponding to at least one of: a data to monitor, a type of data to monitor, a frequency to monitor data, or a selection of devices used to monitor.

In Example 10, the system of any one or more of Examples 1-9 are optionally configured such that the clinician message is formed at least in part using the patient's physiological data.

In Example 11, the system of any one or more of Examples 1-6 are optionally configured comprising a clinician communication device, coupled to the patient communication device, and configured to: present, to a clinician, the patient's negative response; receive a clinician message from the clinician, the clinician message being in response to the presentation of the patient's physiological data; and communicate with patient communication device to revise at least one of the exercise regimen or the second monitoring mode.

In Example 12, the system of Examples 11 is optionally configured such that the patient communication device revises the exercise regimen by revising at least one of: an intensity of an exercise, a frequency of an exercise, a duration of an exercise, a type of exercise, or a specified exercise.

In Example 13, the system of any one or more of Examples 11 or 12 are optionally configured such the patient monitor uses the clinician message to revise an aspect of the second monitoring mode corresponding to at least one of: a data to monitor, a type of data to monitor, a frequency to monitor data, or a selection of devices used to monitor.

In Example 14, the system of any one or more of Examples 11-13 are optionally configured such that the clinician message is formed at least in part using the negative response.

Example 15 describes a method comprising monitoring a patient's physiological data received from a patient-monitoring device, the monitoring including using a first monitoring mode; presenting, to a patient, an option to perform an exercise regimen; receiving a response from the patient indicating whether the patient will perform the exercise regimen; when the response indicates that the patient will perform the exercise regimen: activating a second monitoring mode; detecting that the exercise regimen is complete; and re-establishing the first monitoring mode after the exercise regimen is complete; and when the response indicates that the patient will not perform the exercise regimen: recording the response as a negative response; and repeatedly presenting the option to perform the exercise regimen to the patient.

In Example 16, the method of Example 15 is optionally performed such that the monitoring of the patient's physiological data is performed repeatedly at intervals of time.

In Example 17, the methods of any one or more of Examples 15 or 16 are optionally performed such that the patient-monitoring device includes an implantable medical device.

In Example 18, the methods of any one or more of Examples 15-17 are optionally performed such that the monitoring of the patient's physiological data includes receiving the patient's physiological data at a central system; and storing the patient's physiological data at the central system.

In Example 19, the methods of any one or more of Examples 15-18 are optionally performed such that detecting that the exercise regimen is complete includes receiving and indication from the patient that the patient has completed exercising.

In Example 20, the methods of any one or more of Examples 15-19 are optionally performed such that detecting that the exercise regimen is complete includes using patient physiological data sensed in the second monitoring mode to determine that the patient has completed exercising.

In Example 21, the methods of any one or more of Examples 15-20 are optionally performed comprising presenting, to a clinician, the patient's physiological data captured during the first and second monitoring modes; receiving a clinician message from the clinician, the clinician message being in response to the presentation of the patient's physiological data; and using the clinician message to revise at least one of the exercise regimen or the second monitoring mode.

In Example 22, the methods of any one or more of Examples 15-21 are optionally performed such that the clinician message is formed at least in part using the patient's physiological data.

In Example 23, the methods of any one or more of Examples 15-20 are optionally performed comprising presenting, to a clinician, the patient's negative response; receiving a clinician message from the clinician, the clinician message being in response to the presentation of the patient's physiological data; and using the clinician message to revise at least one of the exercise regimen or the second monitoring mode.

In Example 24, the method of Examples 15-20 and 23 are optionally performed such that presenting the option to perform an exercise regimen to the patient includes presenting a menu including a plurality of exercise regimens, each exercise regimen having a priority level, and each priority level displayed with the menu.

Example 25 includes apparatus comprising means for monitoring a patient's physiological data including using a first monitoring mode; means for presenting, to a patient, an option to perform an exercise regimen; means for receiving a response from the patient indicating whether the patient will perform the exercise regimen; and when the response indicates that the patient will perform the exercise regimen: means for activating a second monitoring mode to monitor the patient's physiological data; means for detecting that the exercise regimen is complete; and means for re-establishing the first monitoring mode after the exercise regimen is complete; and when the response indicates that the patient will not perform the exercise regimen: means for recording the response as a negative response; and means for repeat presenting the option to perform the exercise regimen to the patient.

Example 26 includes a machine-readable medium including instructions which, which when executed by a machine, cause the machine to monitor a patient's physiological data received from a patient-monitoring device, the monitoring including using a first monitoring mode; present, to a patient, an option to perform an exercise regimen; receive a response from the patient indicating whether the patient will perform the exercise regimen; when the response indicates that the patient will perform the exercise regimen: activate a second monitoring mode; detect that the exercise regimen is complete; and re-establish the first monitoring mode after the exercise regimen is complete; and when the response indicates that the patient will not perform the exercise regimen: record the response as a negative response; and repeatedly present the option to perform the exercise regimen to the patient.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. The drawings illustrate, generally, by way of example, but not by way of limitation, various examples discussed in the present document.

DETAILED DESCRIPTION

System Overview

Figure 1:
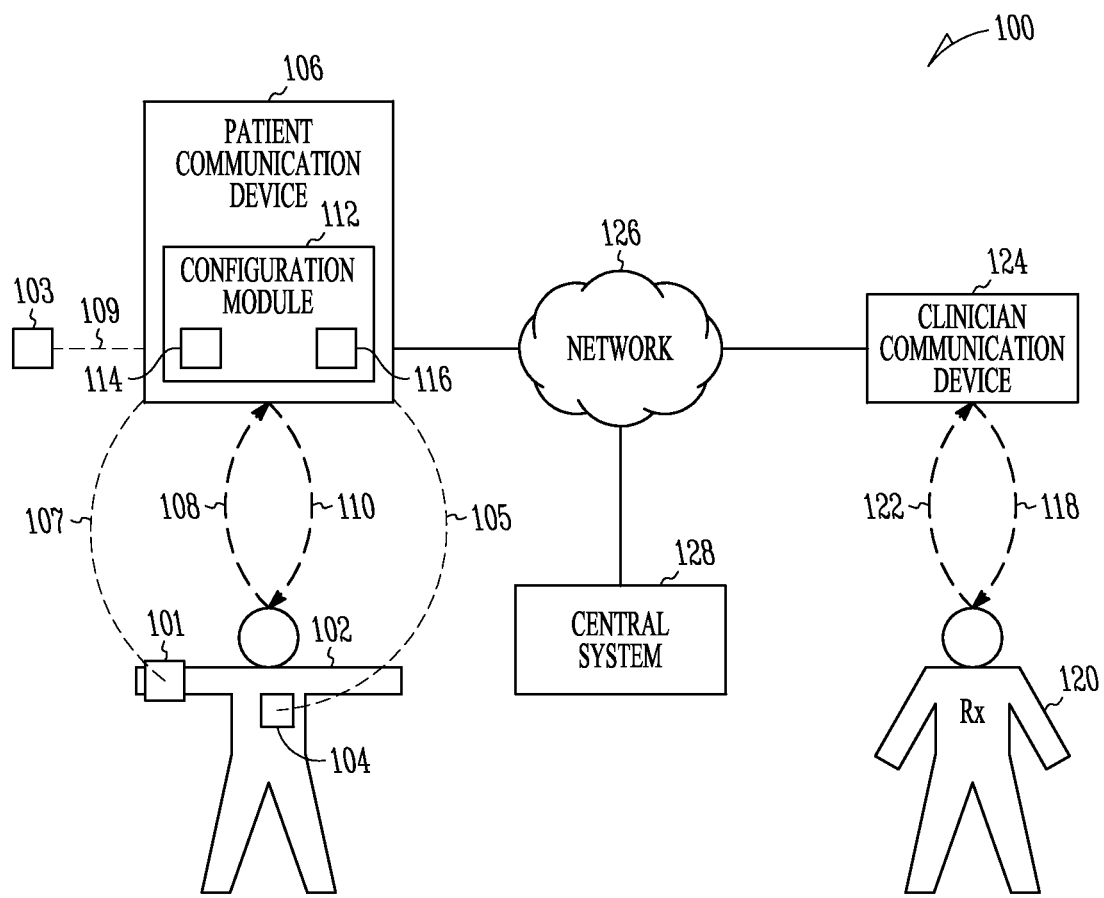
FIG. 1 illustrates portions of a system that enables clinician-patient communication.

FIG. 1 illustrates portions of an example of a system 100 that enables clinician-patient communication. In the example of FIG. 1, the system 100 can include an external patient monitor 101, a patient monitor 104 implanted in a patient 102, and an external environmental sensor 103. The patient 102 can be presented with an option 110 to perform an exercise regimen from a patient communication device 106. The patient 102 sends a response 108 back to the patient communication device 106. A configuration module 112 can be coupled to the patient communication device 106. A monitoring mode module 114 and an exercise regimen module 116 can be coupled to the configuration module 112. In an example, the patient communication device 106 can be communicatively coupled to a central system 128, such as via a network 126. A clinician 120 is presented with data 118 from a clinician communication device 124. In an example, the clinician can send a message 122 using the clinician communication device 124. The message 122 can be displayed on the patient communication device 106. The clinician communication device 124 can be connected to the network 126.

In the example illustrated in FIG. 1, the patient 102 can be provided with an implanted patient monitor 104, an external environmental sensor 103, and an external patient monitor 101, where each device can operate in one or more monitoring modes independent from the other. In an example, the implanted patient monitor 104 includes an implanted medical device. Examples of implantable medical devices can include a pacemaker, an implantable cardioverter defibrillator (ICD), a cardiac resynchronization therapy pacemaker (CRT-P), a cardiac resynchronization therapy defibrillator (CRT-D), a neurostimulation device, a deep brain stimulation device, a cochlear implant, or a retinal implant. The implanted patient monitor 104, in some examples, is configured to monitor patient physiological data in a first monitoring mode and optionally store such data for later communication. Examples of patient physiological data include implantable electrograms, surface electrocardiograms, heart rate intervals (e.g., AA, VV, AV or VA intervals), electrogram templates such as for tachyarrhythmia discrimination, pressure (e.g., intracardiac or systemic pressure), oxygen saturation, activity, heart rate variability, heart sounds, impedance, respiration, intrinsic depolarization amplitude, or the like.

In an example, the external patient monitor 101 can be used to monitor patient physiological data, such as temperature (e.g., a thermometer), blood pressure (e.g., a sphygmomanometer), blood characteristics (e.g., glucose level), body weight, physical strength, mental acuity, diet, or heart characteristics. In examples, external environmental sensor 103 can monitor environmental indicators. Examples of environmental indicators include temperature, air quality, humidity, carbon monoxide level, oxygen level, barometric pressure, light intensity, and sound.

Also, the implanted patient monitor 104 can communicate one or more patient indications to the patient communication device 106. Examples of patient indications can include such things as heart rate, heart rate variability, data related to tachyarrhythmia episodes, hemodynamic stability, activity, therapy history, autonomic balance motor trends, electrogram templates for tachy discrimination, heart rate variability trends or templates, or trends, templates, or abstractions derived from sensed physiological data.

The implanted patient monitor 104, external patient monitor 101, and external environmental sensor 103 are each capable of bi-directional communications 105, 107, 109 with a patient communication device 106. The bi-directional communications 105, 107, 109 can be provided using a hard-wired connection (e.g., serial, USB, Firewire) or a wireless connection (e.g., RF, IR, 802.11g). In examples, the patient communication device 106 sends commands to one or more patient monitors 101, 104 or external environmental sensor 103.

In examples, the patient communication device 106 can be a specialized local computer, a computer terminal, a personal computer, a handheld device such as a personal digital assistant, or a cellular telephone. Coupled to the patient communication device 106 is a configuration module 112. In examples, the configuration module is coupled to a central system 128 or a clinician communication device 124. In some examples, the patient monitor 104 has bi-directional communication directly with the configuration module 112. The communicated information can be physiological data or patient indications, for example. In various examples, the configuration module has a monitoring mode module 114 and an exercise regimen module 116. The exercise regimen module 116 can store exercise regimens, in an example. Additional details of an example exercise regimen are discussed below with reference to FIG. 2. In various examples the monitoring mode module includes entries of monitoring modes. In another example, the configuration module 112 can change the monitoring mode of the patient monitor 104 based on the response 108 from patient 102 that he or she will perform an exercise regimen. Additional details of individual monitoring modes are discussed below with reference to FIG. 2.

In an example, a clinician 120 communicates using a clinician communication device 124. In an example, the clinician communication device 124 can be a specialized local computer, a computer terminal, a personal computer, a handheld device such as a personal digital assistant, or a cellular telephone. The clinician communication device 124 presents patient physiological data 118 to the clinician 120.

In some examples, the network 126 can include one or more wired or wireless networking such as the Internet, satellite telemetry, cellular telemetry, microwave telemetry, or other short or long-range communication networks. In certain examples the clinician's message 122 is communicated to the configuration module 112 through network 126 and is used to create, change, or remove an exercise regimen, such as by interacting or interfacing with the exercise regimen module 116. In other examples the clinician's message 122 is communicated to the configuration module 112 through network 126 and used to create, change, or remove a monitoring mode, such as by interacting or interfacing with the monitoring mode module 114.

In examples, the central system 128 receives physiological data stored on the patient monitor 104. Also, the central system 128 can store exercise regimens and monitoring modes. In another example, central system 128 can store the patient response 108 to the option 110 to perform an exercise regimen.

Exercise Regimens and Monitoring Modes

Figure 2:
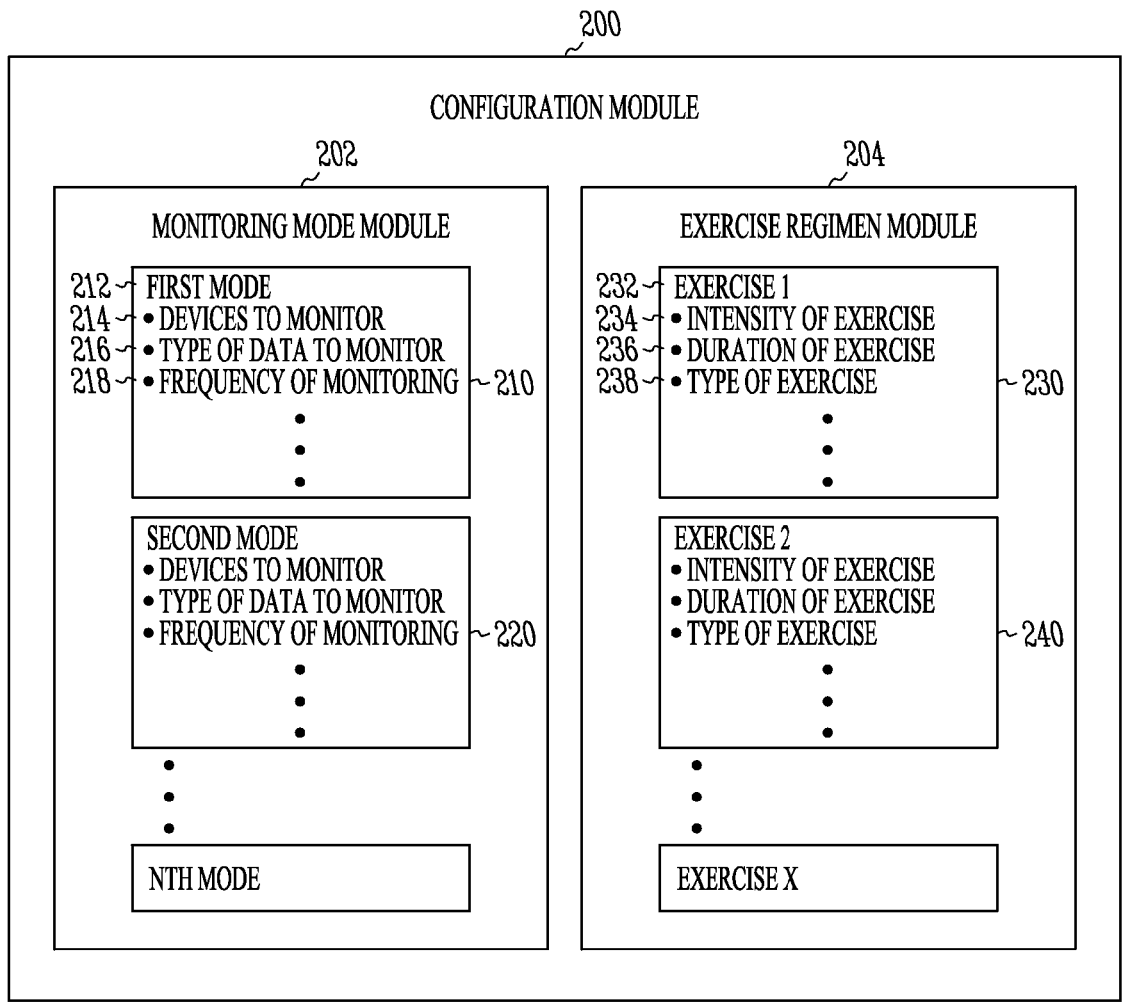
FIG. 2 illustrates portions of a system configured to manage monitoring modes and exercise regimens.

FIG. 2 illustrates portions of an example of a system configured to manage monitoring modes and exercise regimens. The example of FIG. 2 includes a configuration module 200, which can include a monitoring mode module 202 and an exercise regimen module 204. In an example, a monitoring mode module 202 stores at least one entry 210 pertaining to a monitoring mode. In an example, entry 210 includes a name of the monitoring mode 212, one or more devices to monitor 214, a type of data to monitor 216, and a frequency of monitoring 218. In addition, FIG. 2 includes a second monitoring mode entry 220 to illustrate how multiple monitoring modes entries 210, 220 can be stored using the same monitoring mode module 202.

The name of the monitoring mode 212 can be represented using a descriptive alpha-numeric string. In an example, the name of a first monitoring mode can be "standard monitoring mode." For a second monitoring mode, the name can be "treadmill exercise mode," in an example. If a clinician wishes to have a separate monitoring mode for when the patient is sleeping, for example, a monitoring mode can be stored called "sleep monitoring mode."

There are many types of data that can be monitored. For example, heart rate intervals (e.g., AA, VV, AV or VA intervals), oxygen saturation, activity, heart rate variability, heart sounds, impedance, respiration, intrinsic depolarization amplitude, blood pressure, or the like.

One or more devices can be included in the monitoring. The devices can include implanted or external patient monitoring devices or external environmental sensors, such as those described with respect to FIG. 1. In examples, each device can have an independent frequency of monitoring, or monitoring interval. For example, an external environmental sensor can monitor the ambient temperature of the room every five minutes, an implanted patient monitor can monitor heart sounds every 5 seconds, and an external patient monitor can monitor the patient's body temperature every 30 seconds.

In an example, an exercise regimen module 204 stores at least one entry 230 pertaining to an exercise regimen. In an example, an entry 230 includes a name of the exercise regimen 232, an intensity of the exercise 234, a duration of the exercise 236, and a type of exercise 238. In addition, FIG. 2 includes a second exercise entry 240 to illustrate how multiple exercise entries 230, 240 can be stored using the same exercise regimen module 204. The number of exercise entries is not limited to two, but can include as many as is feasible given other constraints, such as memory size, processor power, data transmission limitations, and the like.

The name of the exercise regimen 232 can be represented using a descriptive alpha-numeric string. In an example, the name of an exercise regimen can be "light treadmill regimen" or "moderate walking regimen." In an example, the intensity of the exercise 234 can be identified qualitatively such as "light," "moderate," or "heavy." The intensity of the exercise 234 can be identified quantitatively, for example, by setting the speed or the incline grade of a treadmill. In examples, the intensity of the exercise 234 regimen can vary over time, such as changing from the beginning of an exercise session to the end of the session. For example, the intensity can start at a "light" intensity and end at a "moderate" intensity. The duration of the exercise 236 can be measured in hours, minutes, seconds, or other measurements of time. In an example, the duration of the exercise 236 is increased or decreased using one or more previously used exercise durations. For example, in a rehabilitation routine, as a patient grows stronger, an exercise routine can be extended to further increase the patient's endurance. Similarly, as a patient recovers from an injury, particular exercises can be reduced or phased out as an injury or condition improves. The type of exercise 238 can be categorized using specific exercises or exercise groups, in examples. For example, the type of exercise 238 can include specific exercises, such as walking on a treadmill, using a stationary exercise bike, or gardening. As another example, the type of exercise 238 can include exercise groups such as anaerobic exercises, aerobic exercises, water exercises, dry land exercises, stretching exercises, upper-body exercises, lower-body exercises, and the like.

In other examples, entries detailing monitoring modes and exercise regimens are stored in one or more locations. For example, with reference to FIG. 1, the entries can be stored in a central system 128, a patient communication device 106, or a clinician communication device 124. In an example, a clinician can construct a monitoring mode or exercise regimen entry using a clinician communication device 124. Then, the clinician communication device 124 can distribute copies of the entries to a central system 128 and a patient communication device 106 via the network 126. As another example, a clinician 120 can revise a monitoring mode entry or exercise regimen entry. Then, the clinician communication device 124 can synchronize with the central system 128 and the patient communication device 106 via the network 126 to update the corresponding exercise regimen or monitoring mode entries.

Changing Monitoring Modes

Figure 3:
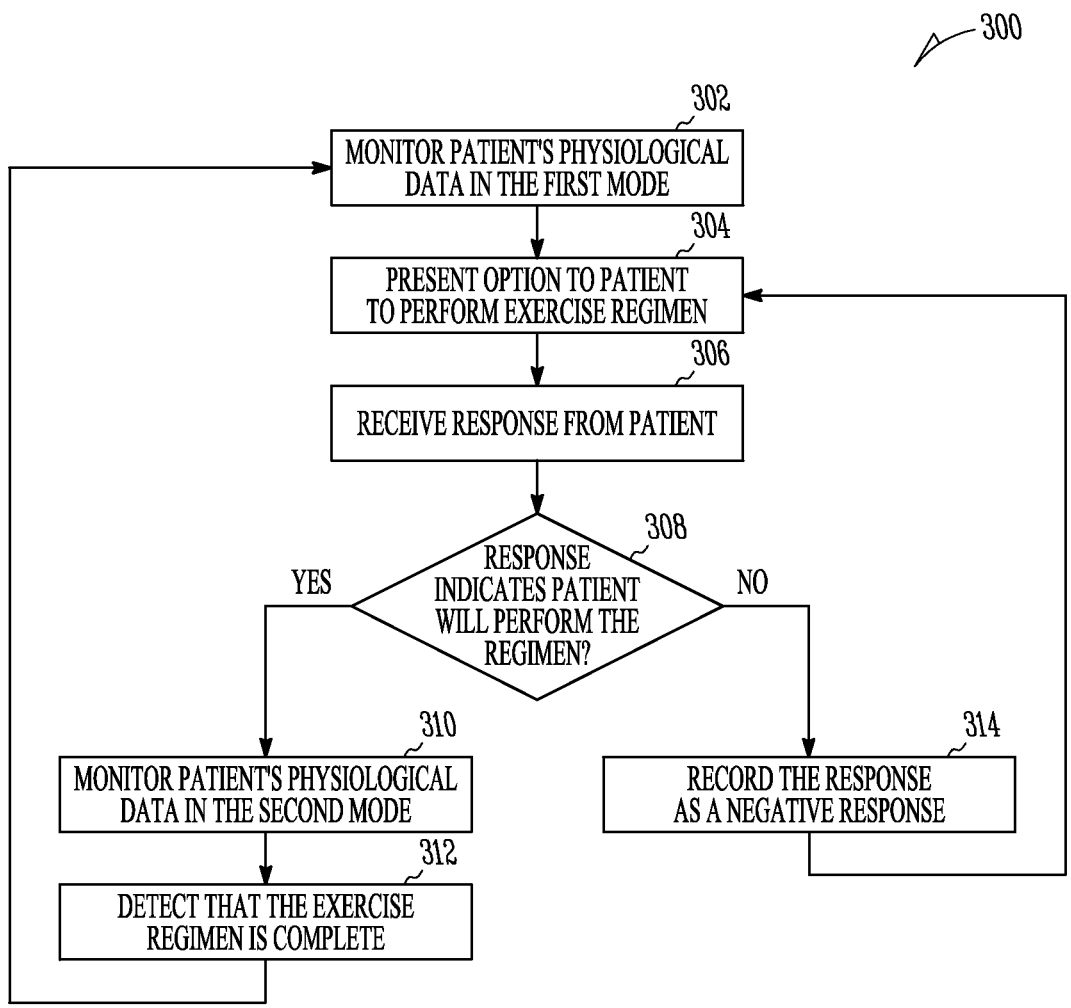
FIG. 3 illustrates an example of a method of changing monitoring modes of a patient monitoring device.

FIG. 3 illustrates an example of a method 300 of changing monitoring modes of a patient monitoring device. In this example, at 302, a patient's physiological data is monitored in a first mode. In an example, the patient's physiological data is collected using an implanted patient monitor (e.g., item 104 in FIG. 1). In an example, the first mode includes monitoring the heart rate of a patient in a periodic manner, using fixed intervals. The period can range from smaller intervals, such as a half a second, to larger intervals, such as three seconds or ten seconds, or more. In another example, the first mode includes monitoring the heart rate of a patient in a recurring manner, using non-fixed intervals. For example, as the heart rate increases (e.g., during exercise) the sampling interval is decreased (e.g., the sampling frequency is increased) to capture a more detailed profile of the patient's heart rhythm.

In other examples, patient physiological data is monitored using one or more external patient monitors (e.g., item 101 in FIG. 1). In an example, the physiological data collected in the first mode can be stored at a central system (e.g., item 128 in FIG. 1).

Figure 9:
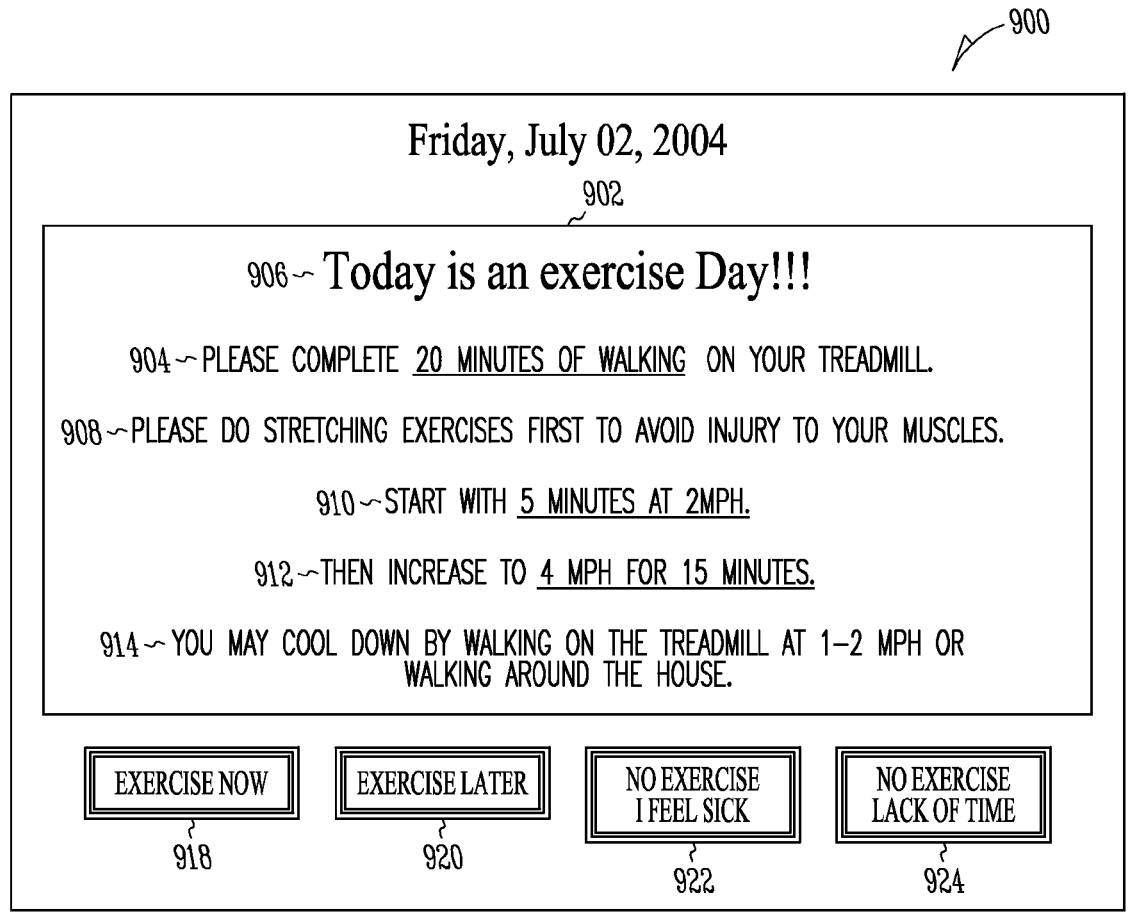
FIG. 9 is an example user interface for presenting an exercise regimen to a patient.

At 304, an option to perform an exercise regimen is presented to a patient. For example, this option can be presented through a monitor connected to a patient communication device such as 106 illustrated in FIG. 1. An example of a user interface to present an option to perform a stored exercise regimen is illustrated in FIG. 9. In an example, the presented option includes presenting a menu of exercise regimens with each regimen having an associated priority level. A clinician can designate a preferred exercise regimen by setting the priority level to a high level (e.g., 10 on a scale of 1 to 10 with 10 being the highest priority). This preferred exercise regimen can be prominently displayed in the menu presented to the patient, such as by highlighting the preferred exercise regimen placing it at the top of a list of exercise regimens, using font or other typographical characteristics to emphasize the exercise regimen, or the like.

At 306, a response indicating whether the patient will perform the exercise regiment is received. In an example where the patient is presented with more than one exercise regimen, the response received can indicate which exercise regimen the patient selected. The response can be received through a patient communication device. In an example, this response can be recorded. In addition to recording the response, current physiological data being recorded in a first mode can be stored with the patient response, in an example. This can allow a clinician to see what a patient was feeling at the time of indicating his or her response.

At 308, it is determined whether the response from the patient indicates that the patient will perform the presented exercise regimen.

When the response indicates that the patient will perform the exercise regimen, then at 310, a second monitoring mode is activated and the patient's physiological data is monitored using the second mode. In an example, the first monitoring mode is disabled before the second monitoring mode begins. This can include pausing or stopping the monitoring of certain types of physiological data or stopping certain devices from monitoring entirely. In another example, the first monitoring mode can be continued while also recording in a second mode. To the extent that there is a conflict between the first and second monitoring modes, one monitoring mode can take priority over the other. In an example, the first monitoring mode can utilize an implantable medical device monitoring the heart rate of a patient every two seconds. The second monitoring mode can utilize the same implantable medical device, but is configured to monitor the heart rate of the patient every second in addition to monitoring environmental data using an external temperature sensor. In this example, because the first and second modes both monitor heart rhythms, the second monitoring mode can take priority over the first monitoring mode such that the heartbeat of the patient is monitored every second.

In an example, an implanted patient monitor (e.g., element 104 in FIG. 1) immediately begins to monitor in a second mode when the patient response indicates an exercise regimen will be completed. In another example, an implanted patient monitor waits a specified amount of time before switching from a first monitoring mode to a second monitoring mode. In a more complex example, the implanted patient monitor can analyze the physiological data in the first mode and wait for an indication that the patient has begun an exercise regimen, such as an increase in activity. In a further example, an implanted patient monitor is configured to wait for a steady state of activity before switching the monitoring mode.

In another example, the data being monitored in the second mode can be recorded and stored on a patient communication device. It can also, at the same time, record the data to a central system (e.g., item 128 in FIG. 1), a clinician communication device (e.g., item 124 in FIG. 1), or an implanted patient monitor (e.g., item 104 in FIG. 1). The monitored data can begin to be recorded when, in one example, the second mode monitoring mode is activated. In an example, the monitored data is not recorded until a steady state of activity is detected.

At 312, the completion of the exercise regimen is detected. An indication that the exercise is complete can be provided by a patient communication or by analyzing the physiological data being monitored. For example, a patient can be provided with a user interface to indicate when the patient is completed with the exercise regimen. In another example, the completion can be automatically detected. For instance, the patient's physiological data can be monitored and when an indication consistent with rest activity is received (e.g., a steady reduced heart rate), the patient's exercise regimen can be considered complete. After completion of the exercise regimen is detected, the first monitoring mode is reestablished and the control flow returns to block 302.

It can be advantageous to know if an exercise regimen has been completed according to the instructions prescribed by a clinician. Therefore, certain examples include detecting compliance with an exercise regimen. In an example, the physiological data recorded from the current exercise regimen can be compared with a previously completed exercise regimen. If the two sets of physiological data are consistent with each other, an indication can be recorded indicating that there is a likelihood that the regimen has been completed according to the prescribed instructions, in an example.

It can be advantageous to have a single record containing all relevant data to an exercise regimen. Therefore, certain examples can include creating an entry in a central system (e.g., item 128 in FIG. 1) that stores a combination of the exercise regimen, the time the patient started the exercise regimen, the time the patient stopped the exercise regimen, compliance with the exercise regimen, physiological data recorded in a first mode, and physiological data recorded in a second mode.

When the response indicates that the patient will not perform the exercise regimen, then at 314, the response is recorded as a negative response. Certain examples include recording the negative response on a central system (e.g., item 128 in FIG. 1). The patient response can contain additional descriptive information. For example, using provided user interface controls, a patient can provide a reason why the exercise regimen will not be performed (e.g., cancel control 922 in FIG. 9, "No Exercise, I feel sick"). In an example, the patient response can be recorded along additional information, such as the time of the response, clinician comments, patient monitor or device states, or other contextual or environmental information.

At 304, an option to perform a stored exercise regimen is presented to a patient again. In examples, the presentation can be delayed, a message can be sent to the clinician, or the exercise regimen can be adaptively changed. In an example, the presentation of the option to perform the exercise regimen is delayed based on the negative response. For example, if the patient indicates he or she feels sick (e.g., cancel control 922 in FIG. 9), the presentation can be delayed for a day. In a further example, a message can be sent to a clinician communication device (e.g. item 124 in FIG. 1) to alert the clinician the patient is sick. In yet another example, based on the response, the exercise routine can be adaptively changed. As an example, a user who is initially provided a moderate exercise routine can be provided a low intensity replacement exercise routine after the moderate exercise routine is declined with the indication that the patient is feeling tired.

In some procedures of remotely-monitored rehabilitation a patient communication device can be configured to retrieve historical patient data and present it to a user. The historical patient data can include previous exercise data to allow the patient to track rehabilitation progress. In an example, the physiological data can be sorted by the viewing patient. The sorting can be organized by activity, regimen, date, or other recorded characteristics of exercise regimens. In an example, an activity goal can be set by a patient or clinician for a given time period and a progress bar can be shown to the patient displaying the amount of activity the patient has completed versus the established goal.

Clinician Modification of Monitoring Modes or Exercise Regimens

Figure 4:
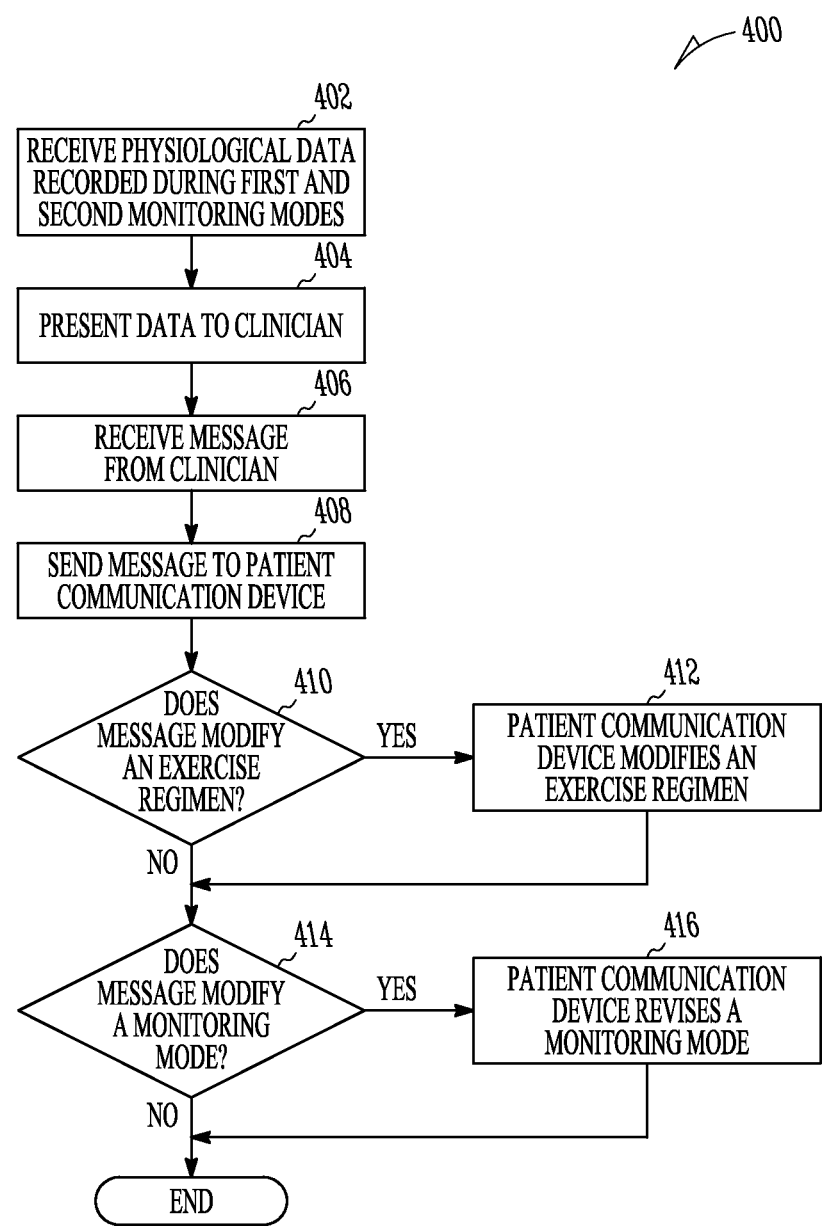
FIG. 4 illustrates an example of a method of a clinician using physiological data to manage a monitoring mode and an exercise regimen.

FIG. 4 illustrates an example of a method 400 of a clinician using physiological data to manage a monitoring mode or an exercise regimen. In this example, at 402, physiological data stored during a first and a second monitoring mode is received. In an example, the data is received from a clinician communication device. In another example, the data is received from a central system, a patient monitor, a configuration module, or a patient communication device.

At 404, the physiological data is presented to a clinician. In an example, the data is presented using a clinician communication device (e.g., element 124 is FIG. 1). In one example, the data retrieved can be sorted by the clinician. The sorting can be organized by activity, regimen, compliance, data, or recorded characteristics of the physiological data.

At 406, a message is received from the clinician. In an example, the message can be formed at least in part using the physiological data. In an example, the message can be formed at least in part using a negative response from a patient. In an example, the message is received at a clinician communication device. In an example, the clinician message can include an informational message, an alert message, a prescription message, an exercise message, a monitoring mode message or a therapy a message. In an example, the exercise message can include instructions to modify an exercise regime. Possible changes can include the duration of an activity, the frequency of an activity, the target heart rate, the percentage of a day the patient should remain active, or settings for a piece of exercise equipment (e.g., treadmill speed, grade, distance, or duration). In another example, the monitoring mode message can include instructions modifying a monitoring mode. Possible changes can include modifying what selection of devices are used in the monitoring, what type of data to monitor for each device, and the frequency at which the data are monitored. The therapy message can include encouragement from the clinician, in one example. In another example, the prescription message can prescribe a drug therapy. An alert message can notify the patient to possible health problems that the clinician has seen in the monitored data.

At 408, the message is sent to a patient communication device. In an example, the message is sent over a network (e.g., item 126 in FIG. 1).

If at 410 it is determined that the message modifies an exercise regimen, then, at 412, the patient communication device modifies an exercise regimen based on the clinician message. In an example, the message is sent to an exercise regimen module such as exercise regimen module 116 in FIG. 1 where the message is analyzed. For example, if the message contains new or revised instructions for an exercise regimen, the instructions can be sent to an exercise regimen module and the corresponding exercise regimen can be updated.

Then at 414, it is determined if the message modifies a monitoring mode. If the messages modifies a monitoring mode then, at 416, the patient communication device revises a monitoring mode based on the clinician message. In an example, the message is sent to a monitoring mode module such as monitoring mode module 114 in FIG. 1 where the message is analyzed. For example, if the message contains a revised selection of devices for a monitoring mode, the message can be sent to a monitoring mode module where the corresponding monitoring mode configuration can be modified.

Example User Interfaces

Figure 5:
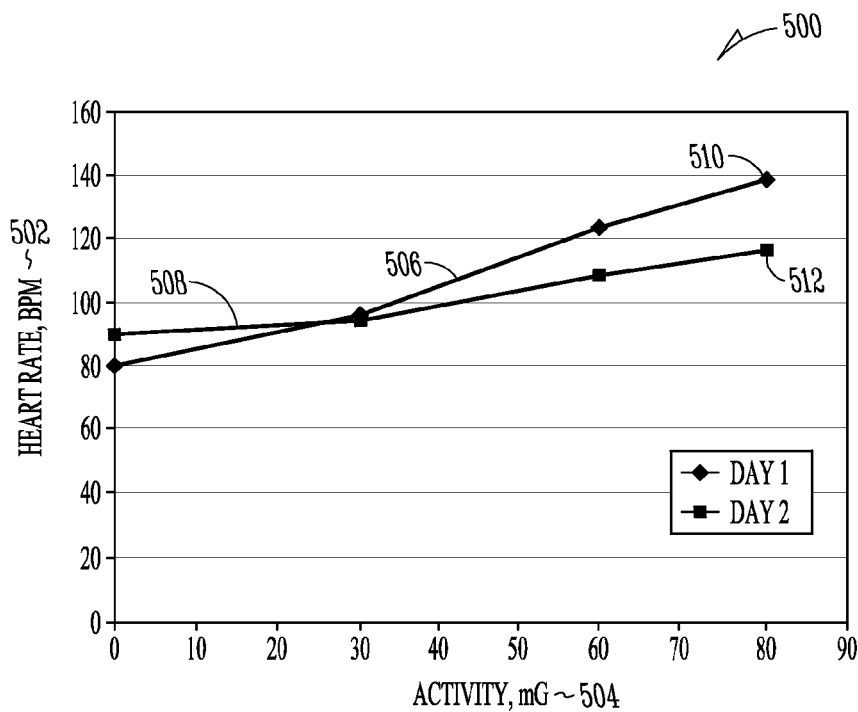
FIGS. 5-8 illustrate example presentations of physiological data.

In some approaches to prescribing exercise regimens, there is no way to easily analyze data recorded over a period of days. Therefore, in some examples, a user can be presented with physiological data recorded on different days. For example, FIG. 5 illustrates an example of a graph 500 plotting heart rate 502 against activity 504. A line 506 represents data monitored on a first day. Another line 508 represents data monitored on a second day. The data points 510 and 512 can include user interface controls that a user can activate to retrieve additional information related to the presented data point 510, 512. For example, the graph 500 can be displayed using a graphical user interface such that if a user clicks on a data point 510, information about the exercise regimen can be displayed allowing the user to analyze the heart rate in relation to a specific exercise.

Figure 6:
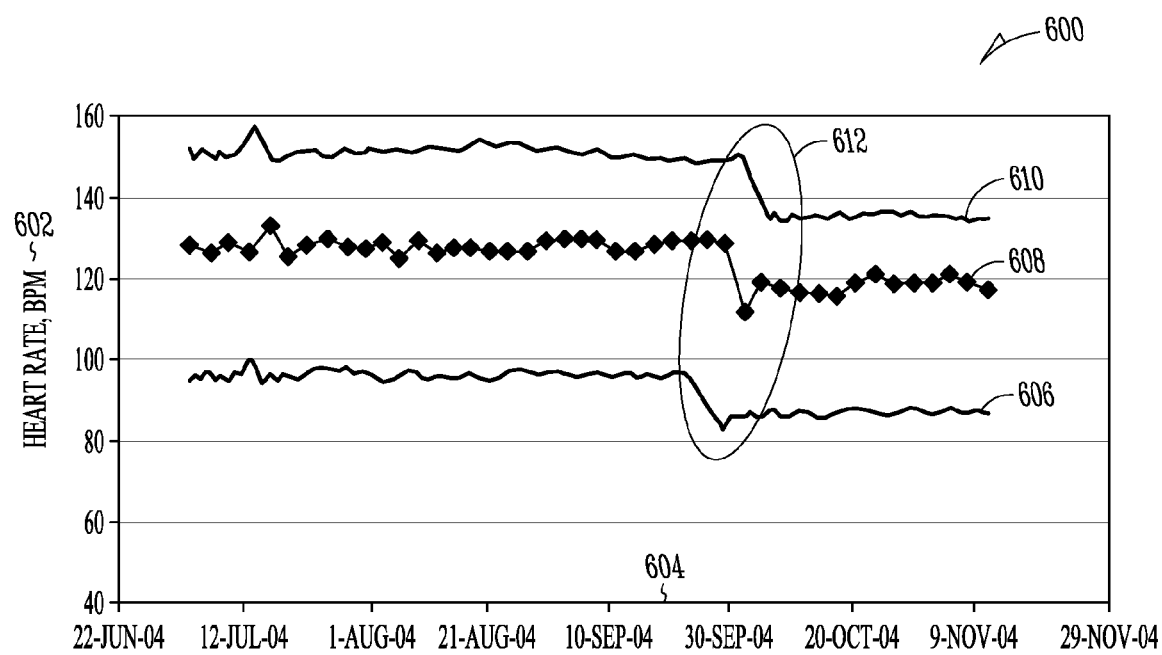

In another example, a graph such as that illustrated in the example of FIG. 6 can be presented to a user. FIG. 6 illustrates an example of a graph 600 plotting heart rate in beats per minute (BPM) 602 against days 604. Data points 606 represent an average or central tendency of a heart rate BPM when the patient is at rest. Data points 608 represent an average or central tendency of a heart rate BPM average when the patient is mildly active. Data points 610 represent an average or central tendency of a heart rate BPM when the patient is moderately active. Presenting this graph 600 to a user can, for example, allow the user to see trends over a longer period of time. In the example shown, the group of points 612 show a substantial drop from one day to the next. This can be used by a clinician to diagnose possible medical complications with the heart such as a decompensation event. As an additional example, the data in the graph 600 can provide a basis for the clinician to prescribe a new therapy or modify an existing therapy. As with the graph 500 illustrated in FIG. 5, the graph 600 in FIG. 6 can be presented using a graphical user interface such that one or more data points can be activated to bring up more physiological or environmental data recorded at that particular time.

Figure 7:
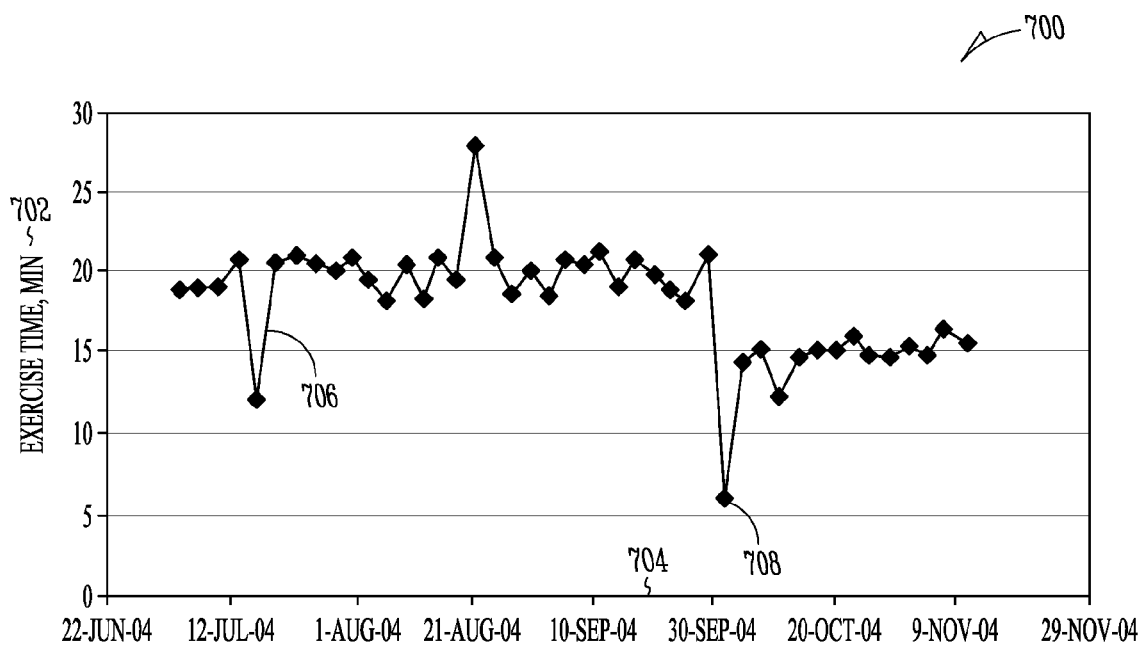

FIG. 7 illustrates an example of a graph 700 plotting exercise time in minutes 702 against days 704. Data points 706 represent the amount of minutes a day a patient has exercised. A drop can be seen at point 708. A clinician, for example, can activate point 708 to view detailed information about the exercise regimen that was being performed to help understand the drop. In a further example, the clinician can use a chart such as the graph 600 illustrated in FIG. 6 to further diagnose any possible medical complications.

As discussed, individual data points in FIGS. 5-7 can be activated to bring up more information. Additionally, groups of two or more data points can be activated by the user such that a summary, average, central tendency, or aggregate view representing the selected group of data points can be displayed to the user.

Figure 8:
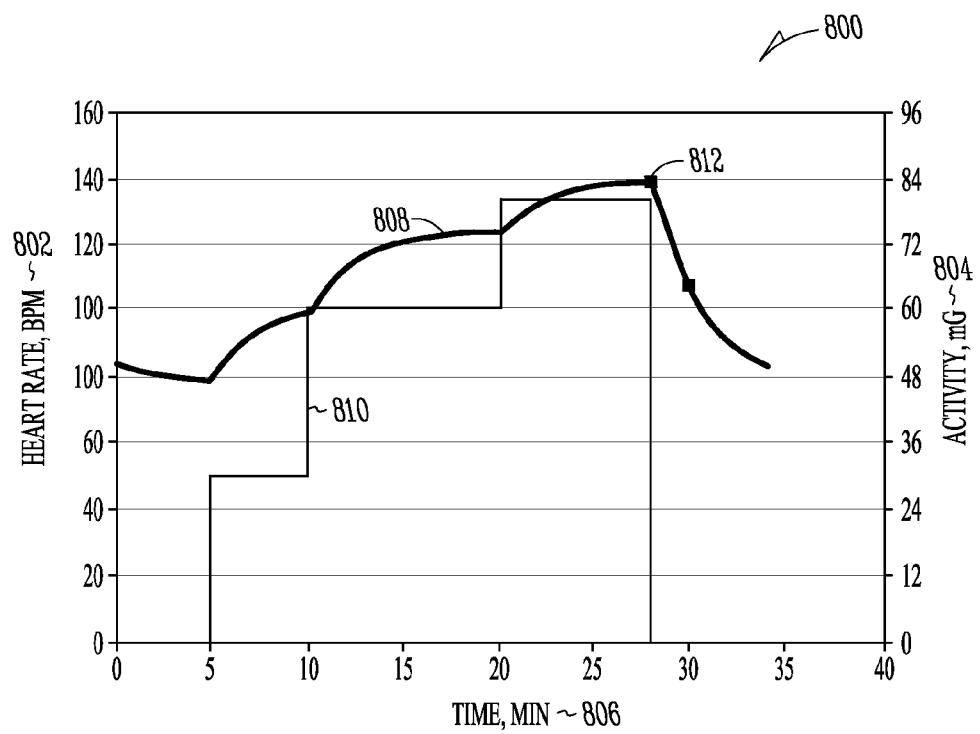

FIG. 8 an example of a chart that can be presented to a user. The example of FIG. 8 illustrates heart rate 802 and activity level 804 plotted against time in minutes 806. Line 808, represents the heart rate data and line 810 represents activity levels from, for example, an activity sensor. In another example, a clinician can hover over a line 808 and get more information such as the heart rate response as shown at point 812.

FIG. 9 illustrates an example of a user interface 900 for presenting an exercise regimen to a patient. In an example, instructions 902 can include a day, a type of exercise, a duration of exercise, a cool-down routine, and an intensity of workout. In an example, the presentation of an exercise regimen 904 will include an activity the patient is requested to perform. The instructions 902 can include an informational banner 906, which can inform the patient that the current day is an exercise day. The instructions 902 can further include warm-up information 908, such as stretching before commencing any exercise. In an example, the exercise regimen 904 can be tailored to walking on a treadmill. The exercise regimen can further specify a total time for walking on the treadmill. In addition, the instructions 902 can specify an initial exercise pace 910, such as a target speed and duration of walking. In addition, the instructions 902 can provide interval training instructions 912, for example, when to increase the speed or duration of an exercise. In an example, the instructions 902 can provide cooling down instructions 914, which can specify what to do after the regimen is completed.

In an example, user interface 900 includes one or more input controls 918, 920, 922, 924 that can be used to respond to the patient instructions 902. The input controls 918, 920, 922, 924 can include an affirmation control 918, a delay decision control 920, and cancel controls 922, 924. The affirmation control 918 can be used to indicate that the patient will perform the exercise routine described in the patient instructions 902 immediately or within a reasonably short time after affirming. The delay decision control 920 can be used to indicate that the patient is unwilling or unable to perform the provided exercise routine, but intends to do so in a reasonable time frame. The cancel controls 922, 924 can be used by the patient to indicate that the patient will not perform the exercise routine provided. In examples, the patient can indicate a reason or reasons why the exercise routine is delayed or canceled. The use of the cancel control 922 indicates the patient will not exercise because he or she feels sick. The use of the cancel control 924 indicates the patient will not perform the exercise because he or she does not have time.

Figure 10:
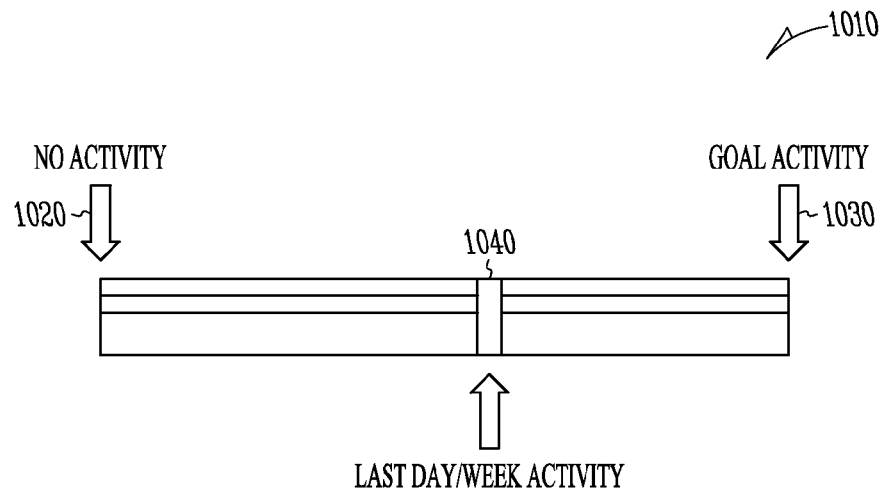
FIG. 10 is an example progress bar.

FIG. 10 illustrates an example of a progress bar 1010. The progress bar 1010 has a range of no activity 1020 to a goal activity level 1030. As discussed in the previous section, this goal activity can be set by the clinician or the patient. In an example, the progress bar 1010 also has a section 1040 that indicates to the patient or clinician the average or central tendency of the activity for the past day, week, or other specified time period.

Figure 11:
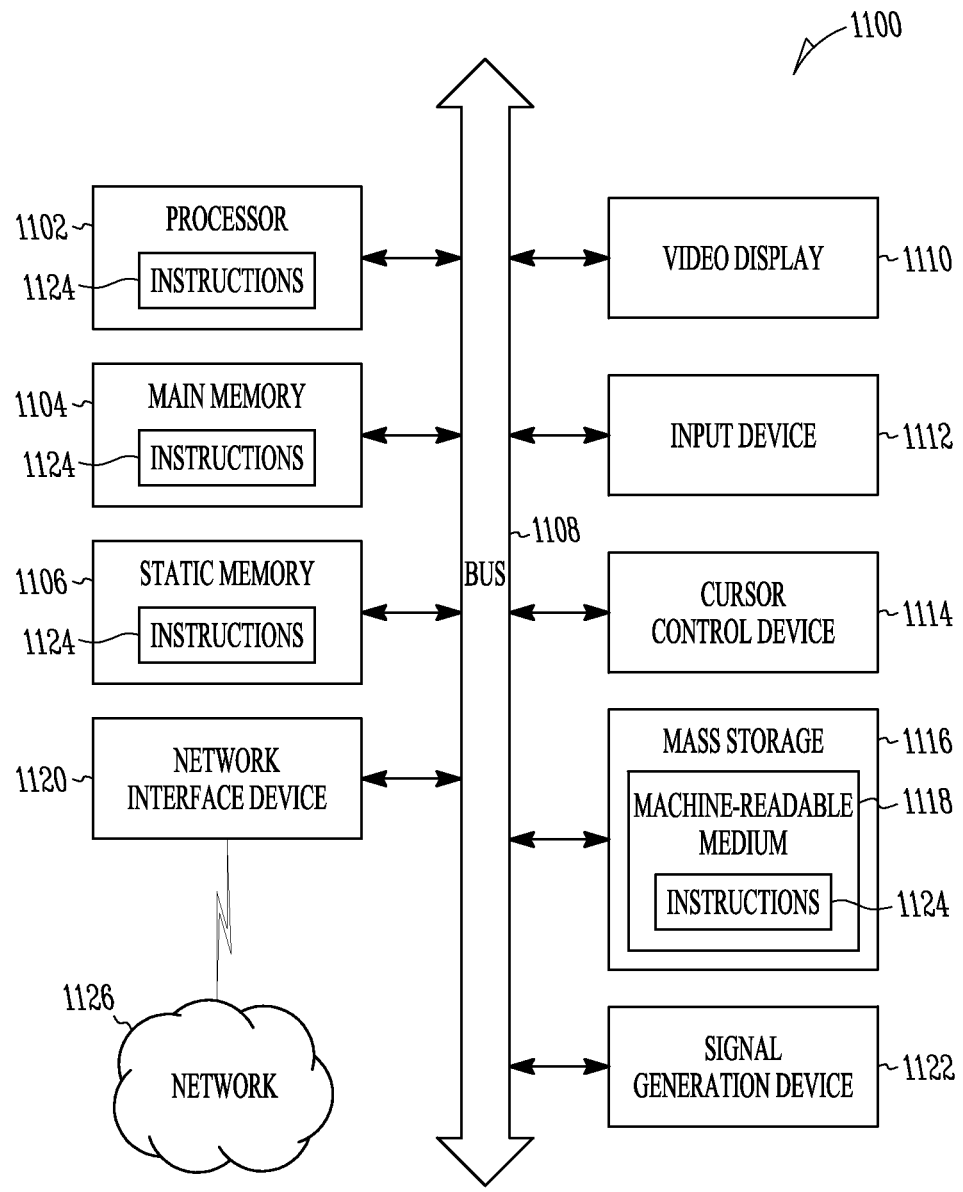
FIG. 11 is an example machine capable of performing the methods described.

FIG. 11 is a block diagram of an article of manufacture, such as machine 1100, in some examples. Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly or C. The software components may communicate using any of a number of mechanisms well known to those of ordinary skill in the art, such as application program interfaces or interprocess communication techniques, including remote procedure calls. The teachings of various examples are not limited to any particular programming language or environment.

Thus, other examples may be realized. For example, an article of manufacture, such as a computer, a memory system, a magnetic or optical disk, some other storage device, and/or any type of electronic device or system may include one or more processors 1102 coupled to a machine-readable medium 1118 such as a memory (e.g., removable storage media, as well as any memory including an electrical, optical, or electromagnetic conductor) having instructions 1124 stored thereon (e.g., computer program instructions), which when executed by the one or more processors 1102 result in performing any of the actions described with respect to the methods above.

Machine 1100 may take the form of a computer system having a processor 1102 coupled to a number of components directly, and/or using a bus 1108. Such components may include main memory 1104, static or non-volatile memory 1106, and mass storage 1116. Other components coupled to the processor 1102 may include an output device 1110, such as a video display, an input device 1112, such as a keyboard, a cursor control device 1114, such as a mouse, and a signal generation device 1122, such as a speaker. A network interface device 1120 to couple the processor 1102 and other components to a network 1126 may also be coupled to the bus 1108. The instructions 1124 may further be transmitted or received over the network 1126 via the network interface device 1120 utilizing any one of a number of well-known transfer protocols (e.g., HTTP). Any of these elements coupled to the bus 1108 may be absent, present singly, or present in plural numbers, depending on the specific example to be realized.

The processor 1102, the memories 1104, 1106, and the mass storage device 1116 may each include instructions 1124 which, when executed, cause the machine 1100 to perform any one or more of the methods described herein. In some examples, the machine 1100 operates as a standalone device or may be connected (e.g., networked) to other machines. In a networked environment, the machine 1100 may operate in the capacity of a server or a client machine in server-client network environment, or as a peer machine in a peer-to-peer (or distributed) network environment. The machine 1100 may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine 1100 is illustrated, the term "machine" shall also be taken to include any collection of machines that individually or jointly execute a set (or multiple sets) of instructions to perform any one or more of the methodologies discussed herein.

While the machine-readable medium 1118 is shown as a single medium, the term "machine-readable medium" should be taken to include a single medium or multiple media (e.g., a centralized or distributed database, and/or associated caches and servers, and or a variety of storage media, such as the processor 1102 registers, memories 1104, 1106, and the mass storage device 1116) that store the one or more sets of instructions 1124. The term "machine-readable medium" shall also be taken to include any medium that is capable of storing, encoding or carrying a set of instructions for execution by the machine and that cause the machine to perform any one or more of the methodologies of the present invention, or that is capable of storing, encoding or carrying data structures utilized by or associated with such a set of instructions. The term "machine-readable medium" shall accordingly be taken to include tangible media, such as solid-state memories and optical and magnetic media.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
    a patient monitor configured to monitor a patient's physiological data using a first monitoring mode;
    a patient communication device configured to:
        present, to a patient, an option to perform an exercise regimen, the option including at least one response option indicating the patient will perform the exercise regimen and at least one response option indicating the patient will not perform the exercise regimen; and
        receive a response to the presented option from the patient indicating whether the patient will perform the exercise regimen; and
    a configuration module, coupled to the patient communication device, the configuration module configured to,
        when the response to the presented option indicates that the patient will perform the exercise regimen:
            activate a second monitoring mode of the patient monitor;
            detect that the exercise regimen is complete; and
            re-establish the first monitoring mode after the exercise regimen is complete; and
        when the response to the presented option indicates that the patient will not perform the exercise regimen:
            receive from the patient, a reason why the patient will not perform the exercise regimen;
            record the response to the presented option as a negative response with the received reason; and
            repeat presenting the option to perform the exercise regimen to the patient.

2. The system of claim 1, wherein the patient monitor is configured to monitor the patient's physiological data repeatedly at intervals of time.

3. The system of claim 1, wherein the patient monitor includes an implantable medical device.

4. The system of claim 1, wherein the patient monitor is configured to:
    receive the patient's physiological data at a central system; and
    store the patient's physiological data at the central system.

5. The system of claim 1, wherein the configuration module is configured to detect that the exercise regimen is complete by receiving an indication from the patient that the patient has completed exercising.

6. The system of claim 1, wherein the configuration module is configured to use patient physiological data sensed in the second monitoring mode to determine that the patient has completed exercising.

7. The system of claim 1, comprising:
    a clinician communication device, coupled to the patient communication device, and configured to:
        present, to a clinician, the patient's physiological data captured during the first and second monitoring modes;
        receive a clinician message from the clinician, the clinician message being in response to the presentation of the patient's physiological data; and
        communicate with patient communication device to revise at least one of the exercise regimen or the second monitoring mode based on the clinician message.

8. The system of claim 7, wherein the patient communication device is configured to revise the exercise regimen by revising at least one of: an intensity of an exercise, a frequency of an exercise, a duration of an exercise, a type of exercise, or a specified exercise.

9. The system of claim 7, wherein the patient monitor is configured to use the clinician message to revise an aspect of the second monitoring mode corresponding to at least one of: a data to monitor, a frequency to monitor data, or a selection of devices used to monitor data.

10. The system of claim 7, wherein the clinician message is formed at least in part using the patient's physiological data.

11. The system of claim 1, comprising
a clinician communication device, coupled to the patient communication device, and configured to:
   present, to a clinician, the patient's negative response;
   receive a clinician message from the clinician, the clinician message being in response to the presentation of the patient's physiological data; and
   communicate with patient communication device to revise at least one of the exercise regimen or the second monitoring mode.

12. The system of claim 11, wherein the patient communication device is configured to revise the exercise regimen by revising at least one of: an intensity of an exercise, a frequency of an exercise, a duration of an exercise, a type of exercise, or a specified exercise.

13. The system of claim 11, wherein the patient monitor is configured to use the clinician message to revise an aspect of the second monitoring mode corresponding to at least one of: a data to monitor, a frequency to monitor data, or a selection of devices used to monitor.

14. The system of claim 11, wherein the clinician message is formed at least in part using the negative response.

15. The system of claim 1, wherein the option to perform the exercise regimen is presented on a day associated with the exercise regimen.

16. The system of claim 15, wherein the exercise regimen is requested by a clinician communication device.

17. The system of claim 1, wherein the exercise regimen is presented in a list of exercise regimens.

18. The system of claim 17, wherein each exercise regimen in the list of exercise regimens is associated with a priority level and the exercise regimen with the highest priority level is emphasized in the list of exercise regimens.

19. A method comprising:
monitoring a patient's physiological data received from a patient-monitoring device, the monitoring including using a first monitoring mode;
presenting, to a patient, an option to perform an exercise regimen;
receiving a response to the presented option from the patient indicating whether the patient will perform the exercise regimen;
when the response to the presented option indicates that the patient will perform the exercise regimen:
   activating a second monitoring mode of the patent-monitoring device;
   detecting that the exercise regimen is complete; and
   re-establishing the first monitoring mode after the exercise regimen is complete; and
when the response to the presented option indicates that the patient will not perform the exercise regimen:
   receiving from the patient, a reason why the patient will not perform the exercise regimen;
   recording the response to the presented option as a negative response with the received reason; and
   repeatedly presenting the option to perform the exercise regimen to the patient.

20. The method of claim 19, wherein the patient-monitoring device includes an implantable medical device.

21. The method of claim 19, wherein the monitoring of the patient's physiological data includes:
receiving the patient's physiological data at a central system; and
storing the patient's physiological data at the central system.

22. The method of claim 19, wherein the detecting that the exercise regimen is complete includes receiving an indication from the patient that the patient has completed exercising.

23. The method of claim 19, wherein the detecting that the exercise regimen is complete includes using patient physiological data sensed in the second monitoring mode to determine that the patient has completed exercising.

24. The method of claim 19, comprising:
presenting, to a clinician, the patient's physiological data captured during the first and second monitoring modes;
receiving a clinician message from the clinician, the clinician message being in response to the presentation of the patient's physiological data; and
using the clinician message to revise at least one of the exercise regimen or the second monitoring mode.

25. The method of claim 24, wherein the clinician message is formed at least in part using the patient's physiological data.

26. The method of claim 19, comprising
presenting, to a clinician, the patient's negative response;
receiving a clinician message from the clinician, the clinician message being in response to the presentation of the patient's physiological data; and
using the clinician message to revise at least one of the exercise regimen or the second monitoring mode.

27. The method of claim 19, wherein presenting the option to perform an exercise regimen to the patient includes presenting a menu including a plurality of exercise regimens, each exercise regimen having a priority level, and each priority level displayed with the menu.

28. An apparatus comprising:
means for monitoring a patient's physiological data including using a first monitoring mode;
means for presenting, to a patient, an option to perform an exercise regimen;
means for receiving a response to the presented option from the patient indicating whether the patient will perform the exercise regimen; and
when the response to the presented option indicates that the patient will perform the exercise regimen:
   means for activating a second monitoring mode to monitor the patient's physiological data;
   means for detecting that the exercise regimen is complete; and
   means for re-establishing the first monitoring mode after the exercise regimen is complete; and
when the response to the presented option indicates that the patient will not perform the exercise regimen:
   means for receiving from the patient, a reason why the patient will not perform the exercise regimen
   means for recording the response to the presented option as a negative response with the received reason; and
   means for repeating the presentation of the option to perform the exercise regimen to the patient.

29. A non-transitory machine-readable medium including instructions, which when executed by a machine, cause the machine to:
monitor a patient's physiological data received from a patient-monitoring device using a first monitoring mode;
present, to a patient, an option to perform an exercise regimen;
receive a response to the presented option from the patient indicating whether the patient will perform the exercise regimen;
when the response to the presented option indicates that the patient will perform the exercise regimen:

activate a second monitoring mode of the patient-monitoring device;
detect that the exercise regimen is complete; and
re-establish the first monitoring mode after the exercise regimen is complete; and
when the response to the presented option indicates that the patient will not perform the exercise regimen:
receive from the patient, a reason why the patient will not perform the exercise regimen
record the response to the presented option as a negative response with the received reason; and
repeatedly present the option to perform the exercise regimen to the patient.

* * * * *